(12) United States Patent
Ikawa et al.

(10) Patent No.: US 8,393,196 B2
(45) Date of Patent: Mar. 12, 2013

(54) GAS SENSOR

(75) Inventors: Koichi Ikawa, Minokamo (JP);
Masahito Kida, Nagoya (JP);
Shinichiro Kito, Kasugai (JP);
Yoshinori Tsujimura, Kasugai (JP);
Takio Kojima, Ichinomiya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 532 days.

(21) Appl. No.: 12/527,824

(22) PCT Filed: Dec. 12, 2008

(86) PCT No.: PCT/JP2008/072709
§ 371 (c)(1),
(2), (4) Date: Aug. 19, 2009

(87) PCT Pub. No.: WO2009/078370
PCT Pub. Date: Jun. 25, 2009

(65) Prior Publication Data
US 2010/0147685 A1    Jun. 17, 2010

(30) Foreign Application Priority Data
Dec. 14, 2007   (JP) ................................. 2007-323238

(51) Int. Cl.
*G01N 7/00*   (2006.01)
(52) U.S. Cl. ..................................... 73/31.06
(58) Field of Classification Search .................. 73/31.06
See application file for complete search history.

(56) References Cited

U.S. PATENT DOCUMENTS 6,698,283 B2 *  3/2004  Wado et al. ................. 73/204.26
2002/0142478 A1  10/2002  Wado et al.

FOREIGN PATENT DOCUMENTS

| JP | 63-279150 A | 11/1988 |
| JP | 64-17460 U | 1/1989 |
| JP | 3-156354 A | 7/1991 |
| JP | 05-051096 A | 7/1993 |
| JP | 06-027719 A | 4/1994 |
| JP | 09-033470 A | 2/1997 |
| JP | 09-229840 A | 9/1997 |
| JP | 2001-091486 A | 4/2001 |
| JP | 2002-286673 A | 10/2002 |
| JP | 2005-164570 A | 6/2005 |
| JP | 2005-226992 A | 8/2005 |
| JP | 3759027 B2 | 3/2006 |
| JP | 3810324 B2 | 8/2006 |
| JP | 2007-139669 A | 6/2007 |
| JP | 2008-209390 A | 9/2008 |

* cited by examiner

*Primary Examiner* — Hezron E Williams
*Assistant Examiner* — Rodney T Frank
(74) *Attorney, Agent, or Firm* — Sughrue Mion, PLLC (57) ABSTRACT

Between a gas sensing layer (4) and a base member (15) composed of a silicon substrate (2) and an insulating coat layer (3), there is formed an adhesion layer 7, to improve the adhesion therebetween, and to prevent separation. The gas sensing layer (4) and sensing electrodes (6) are electrically connected by abutment of a confronting surface (61) of sensing electrodes (6) confronting the gas sensing layer (4) and sides surfaces of the sensing electrodes on both sides, on the gas sensing layer (4), and accordingly the gas sensor properly senses an electric characteristic of the gas sensing layer (4) varied in accordance with a concentration variation of a specified gas. Furthermore, the sensing electrodes (6) are in contact with the gas sensing layer (4), but the sensing electrodes are not in contact with the adhesion layer (7). Therefore, the adhesion layer (7) need not be a complete insulating layer, and it is possible to use, as the adhesion layer, an incomplete insulating film or a conductive film, so that options of the adhesion layer (7) are increased.

10 Claims, 9 Drawing Sheets

GAS SENSOR

TECHNICAL FIELD

The present invention relates to a gas sensor including a gas sensing layer containing a metal oxide semiconductor as a main component.

BACKGROUND ART

There is a known gas sensor which includes a metal oxide semiconductor such as tin oxide ($SnO_2$), supporting noble metal such as platinum (Pt) as a catalyst and which is arranged to sense a concentration change of a measurement gas to be sensed by utilizing an electric characteristic (such as resistance) varied by the measurement gas. In a production method of such a gas sensor, the noble metal is supported in a dispersed state on the surface of the metal oxide semiconductor by calcination after impregnation of metal oxide semiconductor powder in a liquid solution containing the noble metal element (cf. patent document 1, for example).

It is known to achieve a high gas sensitivity to various smells (bad smells, especially) considered to be caused by hydrogen sulfide or mercaptans by the use of a gas sensing layer including a basic metal oxide supported, as catalyst, on a metal oxide semiconductor (cf. patent document 2, for example). However, the basic metal oxide is high in electric resistance, and the structure of the basic metal oxide supported on the metal oxide semiconductor powder individually as in the patent document 1 increases the electric resistance of the gas sensing layer, and makes difficult the circuit design of the gas sensor. It is possible to prevent an increase of the electric resistance of the gas sensing layer with the structure in which the basic metal oxide is supported on the surface of sintered product (gas sensing layer) obtained by sintering the gas sensing layer of metal oxide semiconductor powder (cf. a patent document 3, for example).

The gas sensing layer of such a gas sensor does not react with the measurement gas at normal temperature, and the gas sensing layer becomes activated and reactive to the measurement gas when heated to 200~400° C. Therefore, in general, a heat generating resistor is provided in a base member such as a semiconductor substrate on which the gas sensing layer is formed. However, when the gas sensor is driven at high temperatures by using the heat generating resistor, there is a possibility of separation at the interface between the gas sensing layer and the base member due to a difference in thermal expansion between the gas sensing layer and base member. Moreover, in such a gas sensor, there is a natural demand for increasing the mechanical adhesive strength between the gas sensing layer and base member to obtain a high reliability. Therefore, there are proposed various structures having an adhesion layer formed between the gas sensing layer and the base member. One example proposes a heat type sensor arranged to mitigate heat expansion with a hafnium oxide layer formed between a heater of platinum (Pt) in the form of a thin film resistor and an underlying insulating film (cf. a patent document 4, for example). Another example proposes a gas sensor arranged to mitigate a thermal expansion coefficient by increasing the surface area of an electrode layer by producing concavities and convexities in the surface of the electrode layer on the substrate, and further by providing, between this electrode layer and the gas sensing layer, an intermediate layer of an electrically conductive functionally graded material in which the compositions of the materials of both layers are varied gradually (cf. a patent document 5).

Patent Document 1: JP 63-279150 (A)
Patent Document 2: JP 06-27719 (B)
Patent Document 3: JP 05-51096 (B)
Patent Document 4: JP 2001-91486 (A)
Patent Document 5: JP 09-33470 (A)

DISCLOSURE OF INVENTION

However, though the structure of the heat type sensor proposed by patent document 4 is effective for improving the adhesion between thin films having great contact areas, this structure is not effective between a thick film gas sensing layer and a base member because the contact area is small. The gas sensor proposed by patent document 5 is able to achieve the adhesion between the base member and the gas sensing layer by producing irregularities in the surface of the electrode layer and forming the conductive intermediate layer on the electrode layer. However, since the gas reaction of the measurement gas occurs at the interface between the sensing electrode and the gas sensing layer, an adverse influence might be exerted on the gas sensitivity by the formation of the conductive intermediate layer having a composition different from that of the gas sensing layer, between the electrode layer and the gas sensing layer.

Therefore, the present invention is devised to meet these problems, and it is an object of the present invention to provide a gas sensor adapted to prevent exfoliation of a gas sensing layer from a base member by the use of an adhesion layer and to sense a concentration variation of a specified gas properly without exerting undesired influence on the gas sensitivity.

In a gas sensor comprising a gas sensing layer which is formed on a base member and which includes, as a main component, a metal oxide semiconductor having an electric characteristic which is varied in accordance with variation of a concentration of a specific or given gas in a measurement gas to be tested, the gas sensor according to an embodiment 1 of this disclosure is characterized in that the gas sensor further comprises a pair of sensing electrodes formed on the base member and arranged to sense variation of the electric characteristic of the gas sensing layer, and an adhesive layer contacting with the gas sensing layer, the sensing electrodes being in contact with the gas sensing layer, but not in contact with the adhesive layer; and that the base member includes: a semiconductor substrate formed with an opening portion extending in a thickness direction, an insulating layer which is formed on the semiconductor substrate and which includes a separating wall portion formed at a position confronting the opening portion, a heat generating resistor formed on the separating wall portion, and a protection film formed on the insulating layer to cover the heat generating resistor, the sensing electrodes, the adhesion layer, and the gas sensing layer being formed on the protection layer of the base member.

The gas sensor according to the embodiment 1 has the structure in which the sensing electrodes are in contact with the gas sensing layer but they are not in contact with the adhesion layer. With this structure, it is possible to improve the adhesion between the base member and the gas sensing layer effectively and simultaneously obtain a good gas sensitivity to the specified gas. Furthermore, because the adhesion layer is out of contact with the sensing electrodes, it is not necessary to make the adhesion layer completely insulating, and it is possible to use, as the adhesion layer, an incomplete insulating film or a conductive film, so that the selection of the adhesion layer is widened. Because the adhesion layer is not in contact with the sensing electrodes, it is possible to put the surfaces of the sensing electrodes securely in contact with the gas sensing layer, and hence further improve the gas sensitivity. Moreover, the gas sensing layer is formed on the protection layer so as to confront the heat generating resistor, and the heat generating resistor is formed at the position confronting the opening portion formed in the semiconductor substrate. Therefore, the heat generating resistor can heat the gas sensing layer efficiently for activation, and the gas sensor can sense the concentration variation of the specified gas properly.

The gas sensor of the disclosure may be so configured that the sum of the thicknesses of the insulating layer and the protection layer is smaller than or equal to 2 μm, the surface roughness Ra of a surface of the protection layer is smaller than or equal to 0.03 μm, and the gas sensing layer thicker than 2 μm is formed on the surface of the protection layer.

In this gas sensor, the sum of the thicknesses of the insulating layer and the protection layer is smaller than or equal to 2 μm. Therefore, it is possible to decrease the quantity of heat to be generated by the heat generating resistor. Moreover, the insulating layer and the protection layer are formed, on the semiconductor substrate, by thin film formation, and accordingly the surface of the protection layer on which the gas sensing layer is formed is in the state having a surface roughness Ra of 0.030 μm or less like a mirror surface. However, in this disclosure, the adhesion layer is provided on the protection layer, as mentioned above. This arrangement improves the adhesion between the gas sensing layer and the base member (protection film), and makes it possible to form the gas sensing layer having a thickness greater than or equal to 2 μm, on the surface of the protection layer in the surface state near a mirror surface, with the adhesion being secured.

The gas sensor of this disclosure may be so configured that the mean or mean value of five greatest peak heights from the surface of the protection layer among heights of surface roughness peaks forming convexities of a surface of the adhesion layer as viewed in a section extending in the thickness direction of the adhesion layer is greater than the sum of thicknesses of the insulating layer and the protection layer.

In this gas sensor, with the surface condition in which the mean of five greatest peak heights among the heights of surface roughness peaks of the adhesion layer from the surface of the protection layer as viewed in a section extending in the thickness direction of the adhesion layer is greater than the sum of thicknesses of the insulating layer and the protection layer, the concavities and convexities of the adhesive layer are made greater, and the adhesion of the gas sensing layer can be improved by the anchor effect. In this disclosure, this mean or mean value is defined as a value obtained by averaging the five greatest peak heights from the surface of the protection layer among heights of roughness peaks forming convexities in the surface of the adhesion layer (rectilinear distances in the direction perpendicular to the surface of the protection layer) as viewed in a section obtained by cutting the base member of the gas sensor inclusive of the adhesion layer by a plane extending in the thickness direction, and magnified by a predetermined magnification with a scanning electron microscope.

The gas sensor of this disclosure may be so configured that the sum of thicknesses of the insulating layer and the protection layer is smaller than or equal to 2 μm, the surface roughness of a surface of the protection layer is smaller than or equal to 0.030 μm, and the gas sensing layer having a thickness which is greater than 2 μm and which is equal to or greater than the double of the above-mentioned sum is formed on the surface of the protection layer.

In this gas sensor, the total thickness of the insulating layer and protection layer is equal to or smaller than 2 μm. Therefore, it is possible to reduce the quantity of heat to be produced by the heat generating resistor. Furthermore, because the adhesion between the gas sensing layer and the base member (the protection layer) is improved by the adhesion layer, it is possible to form the gas sensing layer having the thickness which is greater than or equal to 2 μm and which is equal to or greater than the double of the above-mentioned sum, on the surface of the protection layer which is in the mirror like surface state having the surface roughness Ra equal to or smaller than 0.030 μm, with the secured adhesion.

The gas sensor of this disclosure may be so configured that the adhesion layer is formed at least between the sensing electrodes.

In this gas sensor, the adhesion layer is formed between the sensing electrodes at least. The clearance between the sensing electrodes is relatively narrow, so that it is difficult to improve the adhesion between the surface of the base member located between the sensing electrodes and the gas sensing layer. However, with the configuration of this disclosure, it is possible to improve the adhesion effectively between the surface of the base member located between the sensing electrodes and the gas sensing layer.

The gas sensor of this disclosure may be so configured that the sensing electrodes are shaped like the teeth of a comb, the teeth of the sensing electrodes are so arranged that a tooth of one electrode is inserted between two of the teeth of the other, and the adhesion layer is formed between the teeth of one electrode and the teeth of the other electrode.

In this gas sensor, because the sensing electrodes are shaped like the teeth of a comb, the teeth of the sensing electrodes are so arranged that a tooth of one electrode is inserted between two of the teeth of the other, and since the adhesion layer is formed between the teeth of one electrode and the teeth of the other electrode, it is possible to improve the adhesion between the surface of the base member located between the sensing electrodes and the gas sensing layer more effectively.

The gas sensor of this disclosure may be so configured that the adhesion layer is formed continuously in a region between the sensing electrodes and regions surrounding the sensing electrodes.

Because of the adhesion layer formed continuously between the sensing electrodes and around the sensing electrodes, this gas sensor can improve the adhesion between the base member and the gas sensing layer more effectively.

The gas sensor of this disclosure may be so configured that the adhesion layer is an insulating layer.

In this gas sensor, because of the adhesion layer being insulating, the adhesion layer does not exert influence on the electric conductivity of the gas sensing layer, and therefore, the gas sensor can provide a good gas sensitivity to the specified gas.

The gas sensor of this disclosure may be so configured that the material of the gas sensing layer is interposed between particles of the material of the adhesion layer.

In this gas sensor, because of the structure in which the material of the gas sensing layer is interposed between particles of the material of the adhesion layer, it is possible to further improve the adhesion between the adhesion layer and the gas sensing layer and to prevent delamination between the adhesion layer and the gas sensing layer.

The gas sensor of this disclosure may be so configured that the projected area obtained by projecting the contact surface between the gas sensing layer and the adhesion layer, on the base member, from a side (gas sensing layer's side) on which the gas sensing layer formed on the base member is located is greater than or equal to 50% of a projected area obtained by projecting contact surfaces between the gas sensing layer and the adhesion layer and sensing electrodes, on the base member, from the side on which the gas sensing layer is located.

With the structure in which the projected area obtained by projecting the contact surface between the gas sensing layer and the adhesion layer, on the base member, from the side (gas sensing layer's side) on which the gas sensing layer is located is greater than or equal to 50% of the projected area obtained by projecting the contact surfaces between the gas sensing layer and the adhesion layer and sensing electrodes, on the base member, from the side on which the gas sensing layer is located, this gas sensor can provide the adhesion between the base member and the gas sensing layer more reliably.

BEST MODE(S) FOR CARRYING OUT THE INVENTION

The following is explanation on a gas sensor of one embodiment of the present invention, with reference to the drawings. First, the construction of a gas sensor 1 is explained with reference to FIGS. 1~6. An up and down direction is an up and down direction as viewed in FIG. 2, and a left and right direction is a left and right direction in FIGS. 1~6.

Figure 1:
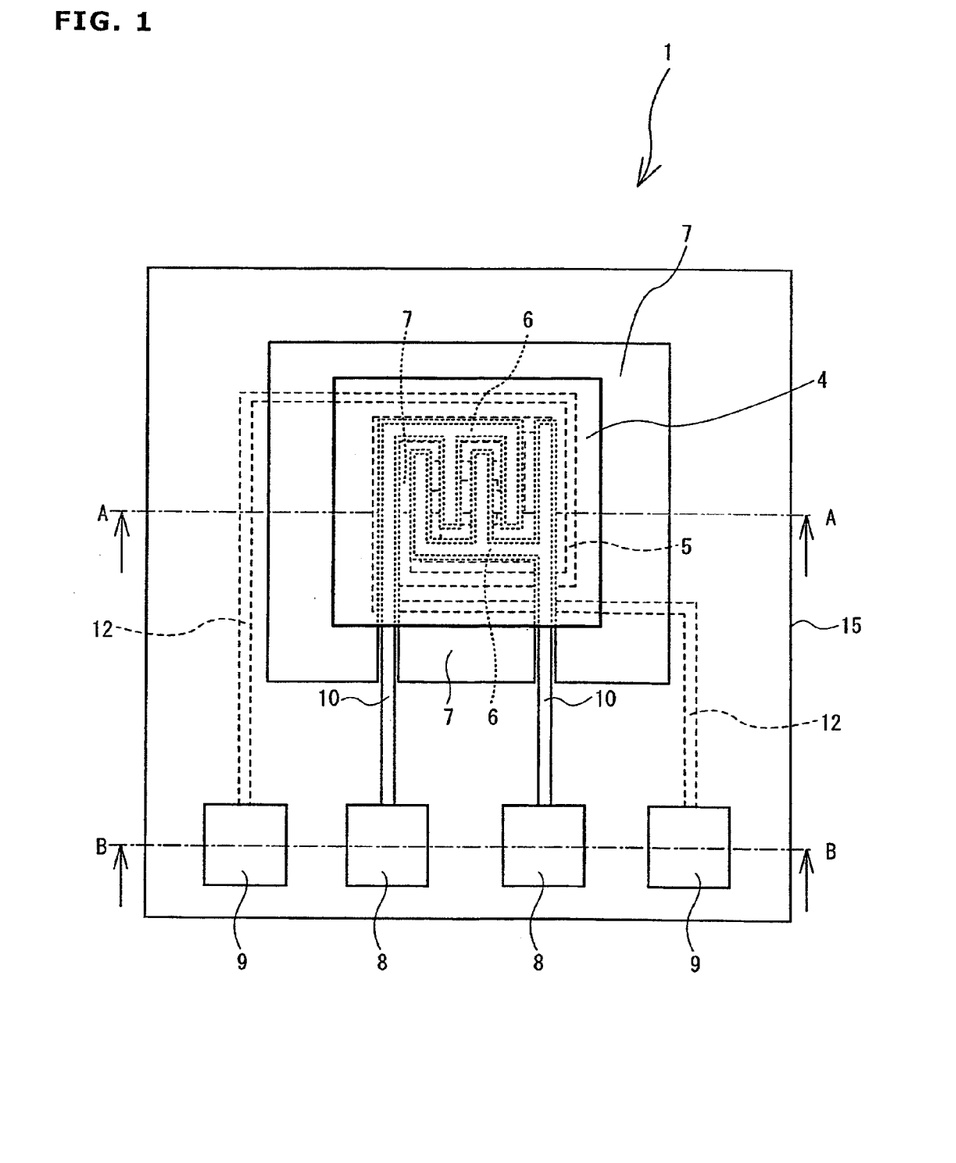
FIG. 1 is a plan view of a gas sensor 1.
Figure 2:
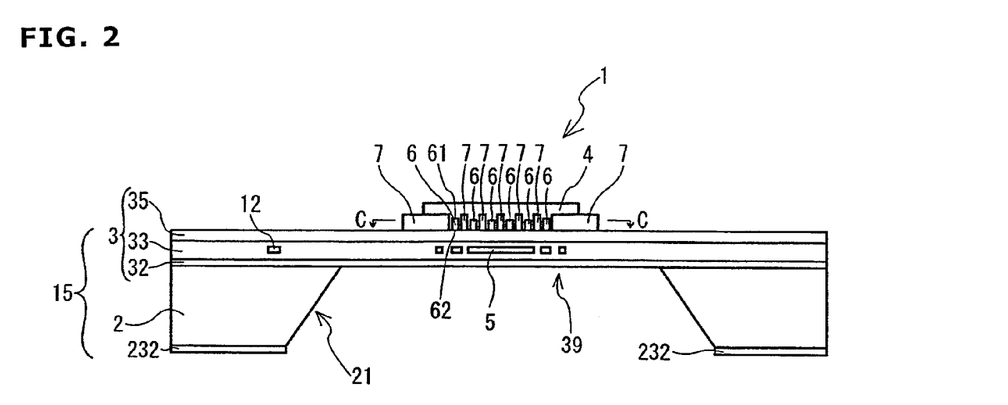
FIG. 2 is a sectional view taken across a line A-A shown in FIG. 1 as viewed in a direction of arrows.

As shown in FIG. 1, gas sensor 1 is a rectangular gas sensor having a flat rectangular shape having a length of 2.6 mm and a width of 2 mm. As shown in FIG. 2, gas sensor 1 has the construction including an insulating coat layer 3 which is formed on an upper surface of a silicon substrate 2, a heat generating resistor 5 which is formed in the insulating coat layer 3, and adhesion layer 7 and gas sensing layer 4 which are formed on an upper surface of the insulating, coat layer 3. Gas sensing layer 4 has such properties that its own electric resistance is varied by a specified gas or predetermined gas in a measurement gas to be tested. In this gas sensor 1, gas sensing layer 4 includes 0.2 weight % calcium oxide contained, as a catalyst, in tin dioxide. By using this gas sensing layer 4, the gas sensor 1 can sense the specified gas such as ammonia ($NH_3$), hydrogen sulfide ($H_2S$), methyl disulfide (($CH_3)_2S_2$), methyl mercaptan ($CH_3SH$), and trimethylamine (($CH_3)_3N$), in the measurement gas mixture. In this invention, the term "sense" means not only to sense the existence or nonexistence of a specified gas contained a measurement gas to be tested, but to sense variation of the concentration of the specified gas as well. Silicon substrate 2 corresponds to "semiconductor substrate" of the present invention, and the silicon substrate 2 and insulating coat layer 3 (base member 15) correspond to "base member" of the present invention. Furthermore, the insulating coat layer 3 corresponds to "insulating layer" of the present invention. Components of gas sensor 2 will be explained more in detail, hereinafter.

As shown in FIG. 2, silicon substrate 2 is in the form of a flat plate of silicon, having a predetermined thickness. An opening portion 21 is formed in the lower surface of silicon substrate 2, by removing part of silicon substrate 2, and a part of an insulating layer 32 is bared, as a separating wall portion 39, by the opening portion 21. Thus, in this gas sensor 1, the silicon substrate 2 including opening portion 21 and the insulating coat layer 3 constitute a base member 15 having a diaphragm structure. This opening portion 21 is so formed that the heat generating resistor 5 buried in an insulating layer 33 is disposed in the separating wall portion 39 in a plan view as viewed from the opening's side of opening portion 21.

Insulating coat layer 3 is composed of insulating layers 32 and 33 and protection layer 35 which are formed on the upper surface of silicon substrate 2. Insulating layer 32 formed on the upper surface of silicon substrate 2 is a film having a predetermined thickness, of silicon nitride ($Si_3N_4$). Part of the lower surface of this insulating layer 32 is bared in the opening portion 21 of silicon substrate 2. The insulating layer 33 formed on the upper surface of this insulating layer 32 is a film having a predetermined thickness, of silicon oxide ($SiO_2$). In this insulating layer 33, there are formed the heat generating resistor 5, lead sections 12 for supplying electricity to heat generating resistor 5, etc. The protection layer 35 in the form of a film having a predetermined thickness, of silicon nitride ($Si_3N_4$) is formed on the upper surface of insulating layer 33. Protection layer 35 is formed so as to cover the heat generating resistor 5 and lead sections 12 for supplying electricity to heat generating resistor 5. Thereby, protection layer 35 functions to protect these portions against contamination and injury. These insulating layers 32 and 33 and protection layer 35 are formed by thin film formation as mentioned later. The surface roughness Ra of the surface of protection layer 35 (that is, the surface on which the gas sensing layer 4 is formed) is lower than or equal to 0.030 μm (in this embodiment, 0.002 μm). Accordingly, the surface of protection layer 35 is in a condition similar to a mirror surface. It is possible to measure the surface roughness Ra of protection layer 35 with a step measuring device made by KLA-Tencor company (device name: SURFACE PROFILER Alpha-Step 500).

Figure 3:
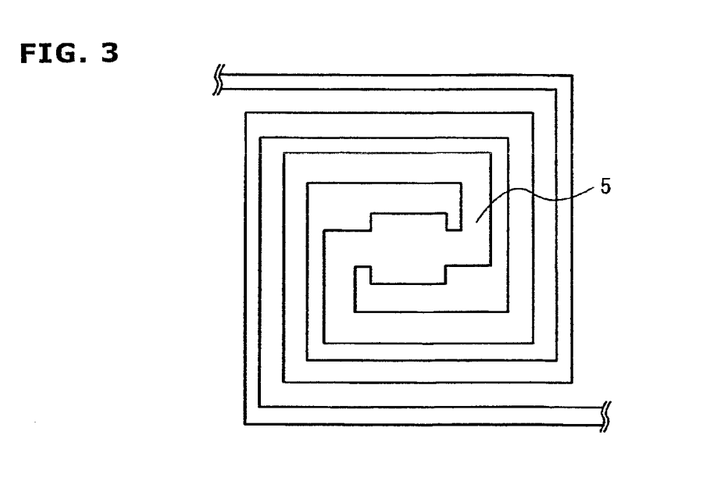
FIG. 3 is a plan view of a heat generating resistor included in the gas sensor 1.
Figure 4:
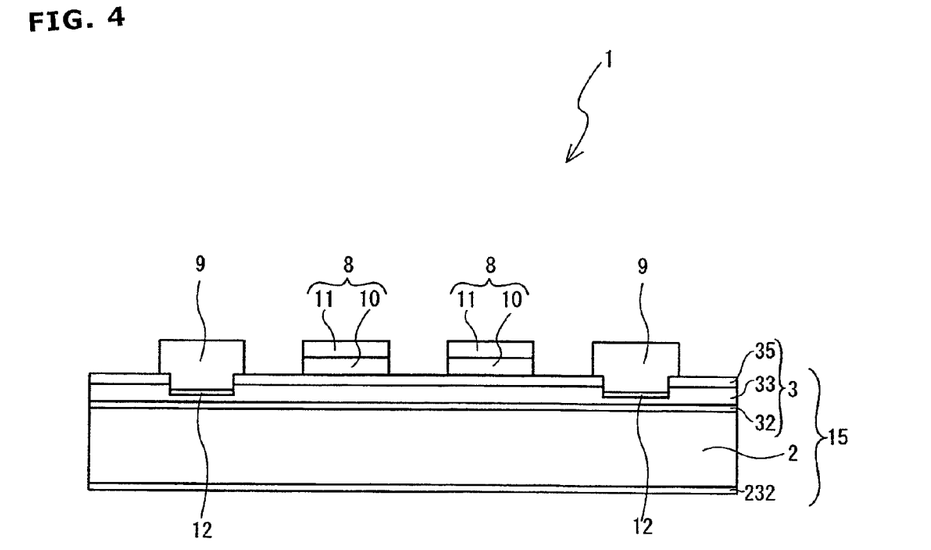
FIG. 4 is a sectional view taken across a line B-B shown in FIG. 1 as viewed in a direction of arrows.

Heat generating resistor 5 is formed in insulating layer 33 at a position corresponding to the upper portion of opening portion 21 of silicon substrate 2, for example, in the form of a spiral in a plan view, as shown in FIGS. 2 and 3. Moreover, lead sections 12 connected with heat generating resistor 5, for supplying electricity to heat generating resistor 5, are buried in insulating layer 33. As shown in FIG. 4, at ends of lead sections 12, there are formed contact pads 9 for connection with an external circuit. Each of heat generating resistor 5 and lead sections 12 has a two-layer structure including a platinum (Pt) layer and a tantalum (Ta) layer. Each contact pad 9 is a pad of gold (Au) formed on the surface of an extraction electrode composed of the platinum (Pt) layer and tantalum (Ta) layer. In gas sensor 1, there are provided a pair of the contact pads 9.

Sensing electrodes 6 and lead sections 10 (cf. FIG. 4) for supplying electricity to the sensing electrodes 6 are formed, on the upper surface of protection layer 35, in the same plane parallel to silicon substrate 2 so that sensing electrodes 6 are located just above heat generating resistor 5. Sensing electrodes 6 and lead sections 10 are formed by a tantalum (Ta) layer formed on protection layer 35, and a platinum (Pt) layer formed on the surface of the tantalum layer. Contact pads 11 of gold (Au) is formed on the surface of lead sections 10 at ends of lead sections 10, and contact pads 11 form oxide semiconductor contact portions 8 for connection with an external circuit, as shown n FIG. 4. In gas sensor 1, there are provided a pair of the oxide semiconductor contact portions 8, as shown in FIGS. 1 and 4.

Figure 5:
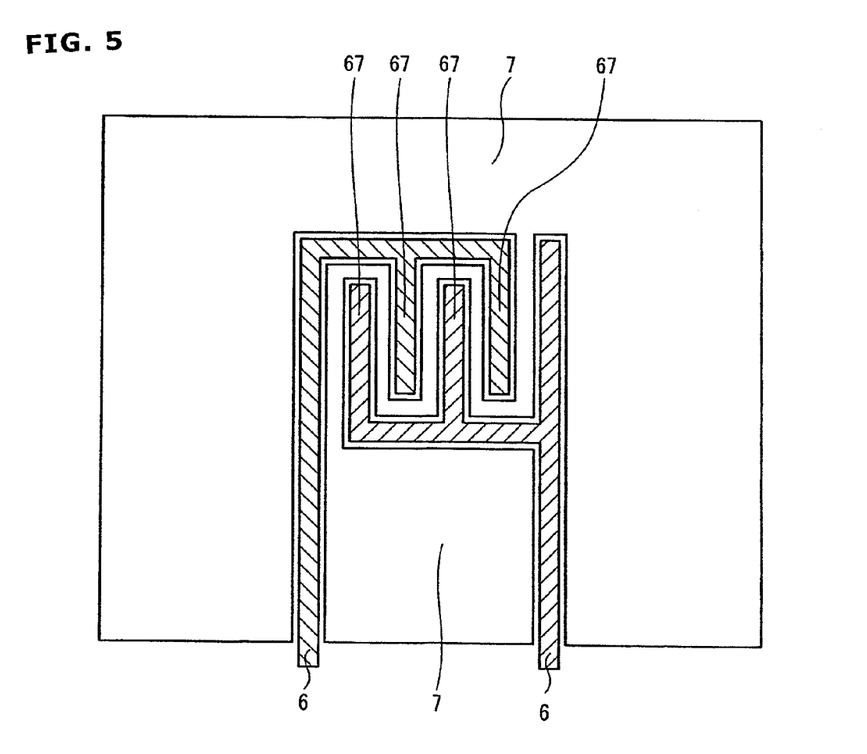
FIG. 5 is a sectional view taken across a line C-C shown in FIG. 2 as viewed in a direction of arrows.

Sensing electrodes 6 have a comb-like planar shape for example, as shown in FIG. 5. Comb teeth 67 of sensing electrodes 6 are interdigitated so that a tooth 67 of one electrode is disposed between teeth 67 of the other. The adhesion layer 7 meanders continuously between the teeth 67 of the first sensing electrode 6 and the teeth 67 of the second sensing electrode 6, with a noncontact clearance or interspace separating the adhesion layer from the teeth 6. The sensing electrodes 6 are arranged in a pair for sensing variation of an electric characteristic in the gas sensing layer 4. As shown in FIG. 5, adhesion layer 7 extends not only in the region between the teeth 67 of sensing electrodes 6, but further extends continuously around the sensing electrodes 6. Adhesion layer 7 is formed so that adhesion layer 7 is separated from the outside borders of the sensing electrodes by a noncontact clearance or interspace. As shown in FIG. 2, each of the sensing electrodes 6 has a confronting surface 61 confronting gas sensing layer 6 and side surfaces between which the surface 61 is formed, and the confronting surface 61 and side surfaces of each sensing electrode 6 abut entirely on the gas sensing layer 4 so that each sensing electrode 6 is electrically connected with gas sensing layer 4. In this way, the confronting surface 61 and side surfaces of each electrode 6 are fully in contact with gas sensing layer 4, so that gas reaction in the interface between gas sensing layer 4 and sensing electrodes 6 is not obstructed at all by other members including adhesion layer 7. Furthermore, heat generating resistor 5 can heat the gas sensing layer 4, and activate gas sensing layer 4 quickly and adequately. From this view point, too, it is possible to improve the gas sensitivity of gas sensor 1. On the other hand, a surface 62 of each sensing electrode 6 confronting protection layer 35 abuts on protection layer 35. Between the adjacent sensing electrodes 6, there is provided the adhesion layer 7 for improving the adhesion of the base member 15 and the gas sensing layer 4, and for preventing exfoliation of gas sensing layer 4 from base member 15 in such a noncontact manner that adhesion layer 7 is not in contact with sensing electrodes 6. Thus, sensing electrodes 6 are in contact with gas sensing layer 4, but sensing electrodes 6 are out of contact with adhesion layer 7.

Figure 6:
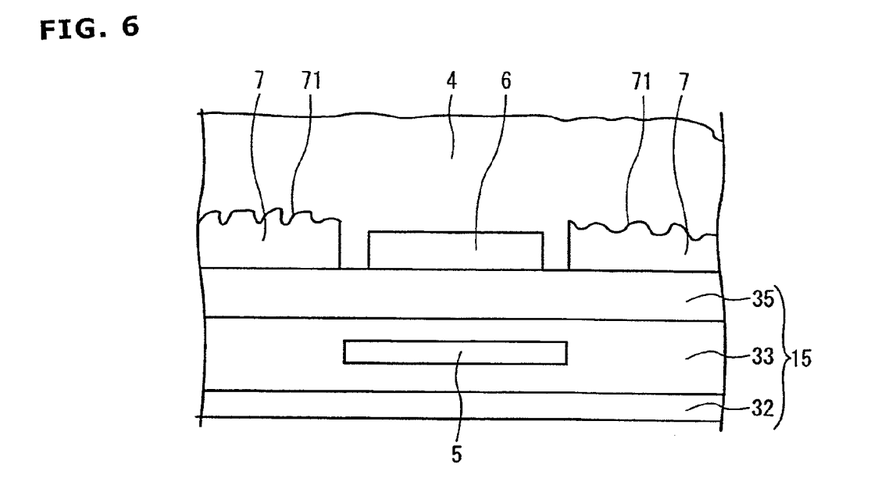
FIG. 6 is an enlarged partial sectional view taken across the line A-A shown in FIG. 1 as viewed in the direction of arrows, showing the vicinity of a gas sensing layer 4.

This adhesion layer 7 is a layer for improving the adhesion between base member 15 and gas sensing layer 4, and adhesion layer 7 has a structure obtained by aggregation of particles of insulating metal oxides, as shown schematically in FIG. 6. Therefore, adhesion layer 7 has an irregular or rugged surface 71. The material of gas sensing layer 4 enters among particles of the material of adhesion layer 7. With this structure, the adhesion between the base member 15 and gas sensing layer 4 in the form of a thicker film is improved. For example, the adhesion layer 7 is formed by forming a hillock Al film by sputtering, and then performing oxidation.

This adhesion layer 7 is formed so as to extend in the region between the comb-shaped sensing electrodes 6 as shown in the lateral sectional view of FIG. 5, and to be out of contact with the peripheries of sensing electrodes 6. Moreover, as shown in the vertical sectional view of FIG. 2, the adhesion layer 7 is not formed between the sensing electrodes 6 and gas sensing layer 4. All the outside surfaces of sensing electrodes 6 abuts on the gas sensing layer 4, except for the surfaces 62. Though the adhesion layer 7 is provided between the adjacent sensing electrodes 6, the sensing electrodes 6 and the adhesion layer 7 are not in contact with each other. This structure improves the adhesion between base member 15 and gas sensing layer 4 without exerting influence on the gas reaction in the interface between the sensing electrodes 6 and the gas sensing layer 4. Moreover, though detachment of the gas sensing layer 4 often starts from an end portion of the gas sensing layer 4, the adhesion layer 7 according to this embodiment is formed around sensing electrodes 6, and the upper surface of adhesion layer 7 contacts with an end portion of gas sensing layer 4. Therefore, this structure can prevent detachment of gas sensing layer 4 from an end portion.

Adhesion layer 7 is not in contact with the sensing electrodes 6. Therefore, it is possible to make the adhesion layer 7 of a material having an electrical conductivity. Preferably, adhesion layer 7 may be made of insulating oxide such as alumina ($Al_2O_3$) and silica ($SiO_2$) in order to prevent influence on the gas reaction in the interface between sensing electrodes 6 and gas sensing layer 4.

A production method of producing the thus-constructed gas sensor 1 is explained with reference to FIGS. 7~13. In the following explanation, an intermediate product of the gas sensor 1 in the process of the production method is called a substrate plate.

(1) Cleaning Silicon Substrate 2

First, a cleaning operation is performed by immersing silicon substrate 2 having a thickness of 400 μm in a cleaning liquid.

(2) Forming Insulating Layer 32 and Insulating Layer 232

Figure 7:
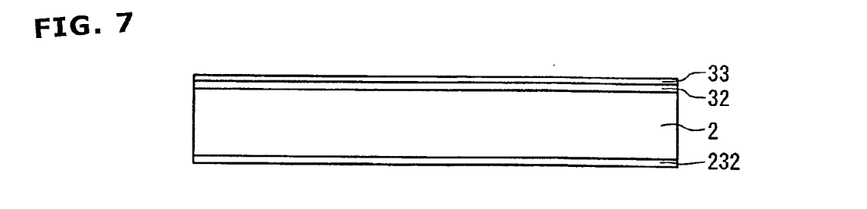
FIG. 7 is a vertical sectional view of the gas sensor 1 in the process of the production method of gas sensor 1.
Figure 8:
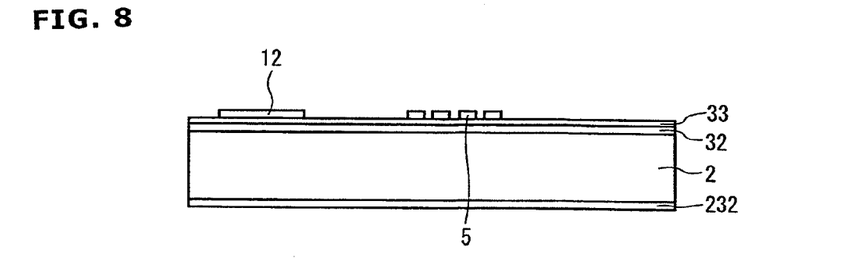
FIG. 8 is a vertical sectional view of the gas sensor 1 in the process of the production method of gas sensor 1.

Next, insulating layer 32 and insulating layer 232 are formed on the upper and lower surfaces of silicon substrate 2, respectively, by LP-CVD by using, as source gas, dichlorosilane ($SiH_2Cl_2$), ammonia (NH3) so that each of insulating layers 32 and 232 is made from a film of silicon nitride ($Si_3N_4$) having a thickness of 200 nm (cf. FIG. 7).

(3) Forming Insulating Layer 33

Then, insulating layer 33 is formed on the surface of insulating layer 32, by plasma CVD by using, as source gas, tetraethoxysilane (TEOS), oxygen ($O_2$) so that insulating layer 33 is made from a film of silicon oxide ($SiO_2$) having a thickness of 100 nm (cf. FIG. 7).

(4) Forming Heat Generating Resistor 5 and Lead Sections 12

Then, by using a DC sputtering system, a layer of tantalum (Ta) having a thickness of 20 nm is formed on the surface of insulating layer 33, and a layer of platinum (Pt) having a thickness of 220 nm is formed on the tantalum layer. After the sputtering operation, patterns of heat generating resistor 5 and lead sections 12 are formed by performing a patterning operation of resist by photolithography, and a wet etching operation with aqua regia (cf. FIG. 8).

(5) Increasing the Film Thickness of Insulating Layer 33

Figure 9:
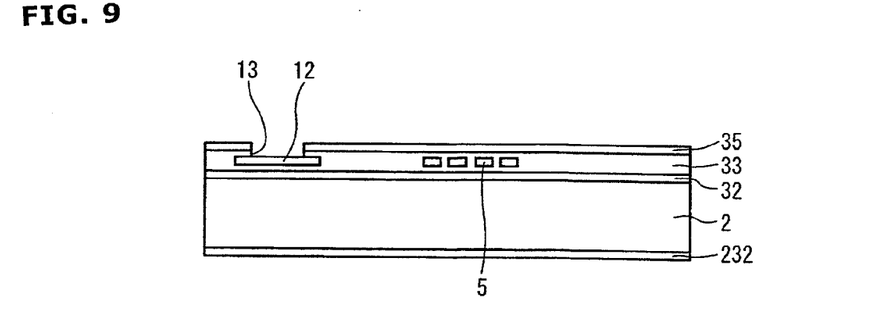
FIG. 9 is a vertical sectional view of the gas sensor 1 in the process of the production method of gas sensor 1.
Figure 10:
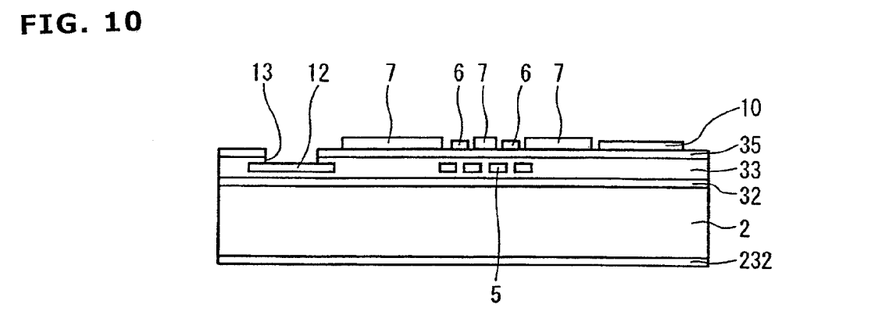
FIG. 10 is a vertical sectional view of the gas sensor 1 in the process of the production method of gas sensor 1.
Figure 11:
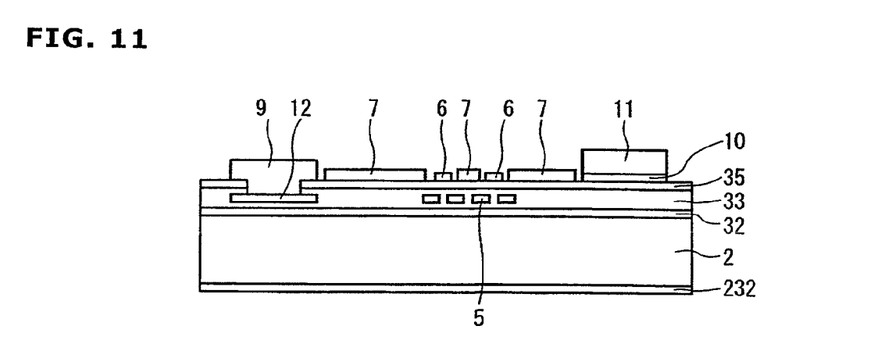
FIG. 11 is a vertical sectional view of the gas sensor 1 in the process of the production method of gas sensor 1.

Then, the film thickness of insulating layer 33 is increased by forming a new insulating layer on the surfaces of insulating layer 33, heat generating resistor 5 and lead sections 12, by plasma CVD by using, as source gas, tetraethoxysilane (TEOS), oxygen ($O_2$) as in the step (3) so that the new insulating layer is made from a film of silicon oxide ($SiO_2$) having a thickness of 100 nm, as shown in FIG. 9. In this way, heat generating resistor 5 and lead sections 12 are buried in the insulating layer 33 having a thickness of 200 nm.

(6) Forming Protection Layer 35

Moreover, protection layer 35 is formed on the upper surface of insulating layer 33, by LP-CVD by using, as source gas, dichlorosilane ($SiH_2Cl_2$), ammonia ($NH_3$) as in step (2) so that protection layer 35 is made from a film of silicon nitride ($Si_3N_4$) having a thickness of 200 nm (cf. FIG. 9).

(7) Forming Holes for Contact Pads 9

Then, contact holes 13 are opened at portions for forming contact pads 9 and thereby the end portions of lead sections 12 are partly bared (cf. FIG. 9) by performing a patterning operation of a resist by photolithography and etching the protection layer 35 and insulating layer 33 by dry etching method.

(8) Forming Sensing Electrodes 6 and Lead Sections 10

Then, by using the DC sputtering system, a layer of tantalum (Ta) having a thickness of 20 nm is formed on the surface of protection layer 35, and a layer of platinum (Pt) having a thickness of 40 nm is formed on the tantalum layer. After the sputtering operation, patterns of comb sensing electrodes 6, lead sections 10 etc. are formed by performing a patterning operation of resist by photolithography, and a wet etching operation with aqua regia (cf. FIG. 10).

(9) Forming Adhesion Layer 7

On the sensing electrodes 6 and protection layer 35, a hillock Al film to form adhesion layer 7 is deposited by sputtering method. Then, after an resist patterning operation by photolithography, the adhesion layer 7 is formed between the comb sensing electrodes 6 and on the protection layer 35 around sensing electrodes 6 (cf. FIG. 10), by removing unwanted Al film on and around the sensing electrodes 6 by a wet etching operation using phosphoric acid as a main component, and then performing oxidation to obtain $Al_2O_3$.

(10) Forming Contact Pads 11, 9

By using the DC sputtering system, a gold (Au) layer having a thickness of 400 nm is formed on the surface of the substrate plate on the electrode's side of the substrate plate formed with the above-mentioned electrode portions. After the sputtering operation, the contact pads 11 and 9 are formed by performing a patterning operation of resist by photolithography and a wet etching operation (cf. FIG. 11).

(11) Forming the Opening Portion 21 (Formation of Diaphragm)

Then, a patterning operation of resist is performed by photolithography and an insulating film serving as a mask is formed by a dry etching operation. Then, the substrate plate is immersed in a solution of tetramethiammonium hydroxide (TMAH), and thereby the opening portion 21 is formed by anisotropic etching of silicon substrate 2 so as to form an opening in the lower surface of silicon substrate 2, and to bare the portion of insulating layer 32 to form the separating wall portion 39 at the position corresponding to the position of heat generating resistor 5 (cf. FIG. 12).

(12) Forming Gas Sensing Layer 4

Figure 12:
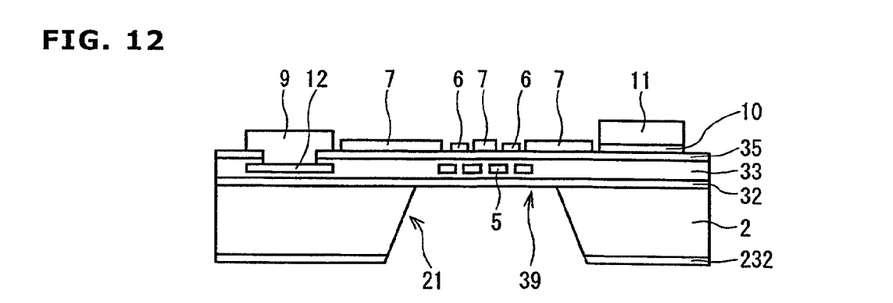
FIG. 12 is a vertical sectional view of the gas sensor 1 in the process of the production method of gas sensor 1.
Figure 13:
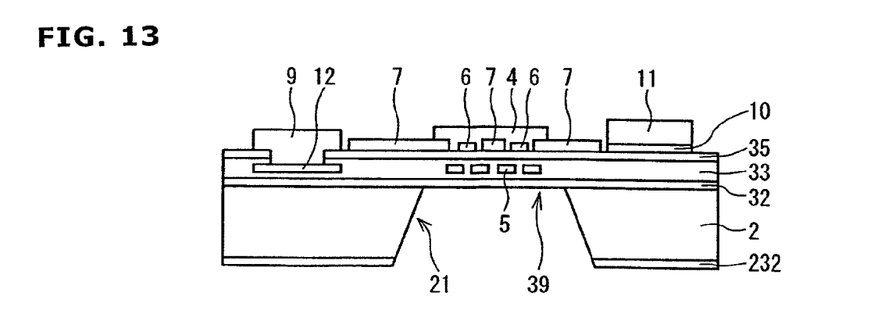
FIG. 13 is a vertical sectional view of the gas sensor 1 in the process of the production method of gas sensor 1.

Furthermore, gas sensing layer 4 is formed by applying, to the sensing electrodes 6 and adhesion layer 7, an oxide semiconductor paste containing tin oxide as a main component and addition of calcium oxide by thick film printing, and thereby forming a paste layer having a thickness of 30 μm (cf. FIG. 12). The oxide semiconductor paste is prepared in the following process. First, tin hydroxide is separated by dissolving tin chloride ($SnCl_2$) in purified water by adding and stirring sufficiently, and thereafter dropping ammonia water. Then, precipitated powder is washed a few times with purified water to remove ammonium ions and chlorine ions, and dried. After drying, the precipitated powder and calcium hydroxide ($Ca(OH)_2$) are dispersed in purified water, followed by sufficient stirring and drying. In this case, the amount of the calcium hydroxide added to the precipitated powder is so determined as to make the weight percent in term of calcium oxide (CaO) equal to 0.2 weight %. After drying, calcination is performed at 800° C. for 5 hours, and the obtained powder in the amount of 5 g is pulverized by a mortar grinder or automatic mortar for one hour. Thereafter, an organic solvent is mixed and the powder is further pulverized for four hours by the motor grinder (or a pot mill). By further performing the pulverization by adding a binder and a viscosity modifier for four hours, a paste having a viscosity of 140 Pa·s at 25° C. is prepared.

(13) Calcining the Substrate Plate

The substrate plate formed with sensing electrodes 6, adhesion layer 7 and gas sensing layer 4 is obtained by calcining the substrate plate at 650° C. for one hour in a heat treating furnace.

(14) Cutting the Substrate Plate

The gas sensor 1 having a planar size of 2.6 mm×2 mm is obtained by cutting the substrate plate with a dicing saw. The thickness (average thickness) of the gas sensing layer 4 of this gas sensor 1 is about 15 μm, as a result of measurement using the above-mentioned step measuring device. By this measurement, it is confirmed that the gas sensing layer 4 having the thickness greater than or equal to the double of the total (600 nm) of the thicknesses of insulating layers 32 and 33 and protection layer 35 is formed contiguously and tightly on the surface of protection layer 35 having a surface roughness Ra equal to or lower than 0.03 μm.

In the above-mentioned fabricating method of the gas sensor 1, it is optional to form a thermally-oxidized film on silicon substrate 2 before step (2) "Forming insulating layer 32 and insulating layer 232". Moreover, though the contact holes 13 are formed in step (7) "Forming holes for contact pads 9", it is optional to form the contact holes 13 after step (8) of "Forming sensing electrodes 6 and lead sections 10". Furthermore, it is optional to omit the operation of oxidizing hillock Al into $Al_2O_3$ in the step (9) of "Forming adhesion layer 7".

As explained above in detail, in the gas sensor 1 according to this embodiment, the confronting surfaces of sensing electrodes 6 confronting the gas sensing layer 4 and the side surfaces of the sensing electrodes 6 abut on the gas sensing layer 4, so that the contact area between the sensing electrodes 6 and gas sensing layer 4 can be secured. Furthermore, sensing electrodes 6 are not in contact with adhesion layer 7. This structure can provide a good gas sensitivity in sensing the specific gas while effectively improving the adhesion between the base member 15 and gas sensing layer 4.

Moreover, sensing electrodes 6 are shaped like a comb, the teeth of sensing electrodes 6 are interdigitated so that one of the teeth 67 of one electrode is disposed between two of the teeth 67 of the other electrode, and the adhesion layer is formed between the teeth 67 of one electrode and the teeth 67 of the other electrode. This arrangement can effectively improve the adhesion between the surface of base member 15 lying between sensing electrodes 6 and the gas sensing layer 4.

Moreover, the gas sensor 1 of this embodiment can provide a novel effect of improving the adhesion between base member 15 and gas sensing layer 4 and at the same time obtaining the good gas sensitivity. Furthermore, since, even if the current supplied to gas sensing layer 4 or the voltage applied to gas sensing layer 4 is decreased, it is possible to sense the concentration variation of the specified gas sufficiently, the gas sensor 1 of this embodiment can provide a secondary effect of making the circuit design of the gas sensor easier and uncostly. Since the heat generating resistor 5 is formed at the position confronting the opening portion 21 formed in silicon substrate 2, the heat generating resistor 5 can heat the gas sensing layer 4 efficiently, and thereby activate the gas sensor to the condition capable of sensing the concentration variation of the specified gas in the measurement gas.

The present invention is not limited to the above-mentioned embodiment. Various variations are possible within the purview of the present invention. For example, at (9) "Forming adhesion layer 7", the adhesion layer 7 is formed by depositing a hillock AL film by sputtering, then removing unwanted Al film around the sensing electrodes 6 by a wet etching operation using phosphoric acid as a main component, after an resist patterning operation by photolithography, and finally performing oxidation to obtain $Al_2O_3$. However, it is optional to form the adhesion layer 7 by other methods such as dip method, electrophoresis method, liquid film transfer method, mist transport method, screen printing method and spin coating method.

Furthermore, instead of forming adhesion layer 7 after the formation of sensing electrodes 6 and lead sections 10, it is optional to form the adhesion layer 7 before the formation of sensing electrodes 7 and lead sections 10. In this case, for example, a sol solution layer to become the adhesion layer 7 is formed, in the form of a film, on the protection layer 35. Thereafter, portions to form sensing electrodes 6 and lead sections 10 are removed by etching or other methods, and then the sensing electrodes 6 and lead section 10 are formed in the removed portions.

Although the insulating coat layer 3 has a multi-layer structure composed of silicon oxide and silicon nitride, it is optional to employ a single layer structure of silicon oxide or silicon nitride. In the above-explained embodiment, heat generating resistor 5 is buried in insulating layer 33. However, the invention is not limited to this arrangement. For example, heat generating resistor 5 may be buried in insulating layer 32.

As a main component of gas sensing layer 4, the embodiment employs tin oxide which is a metal oxide semiconductor. However, it is optional to use other metal oxide semiconductors such as zinc oxide (ZnO), nickel oxide (NiO), titan oxide ($TiO_2$), and vanadium oxide ($VO_2$). As a basic metal oxide to be added to the metal oxide semiconductor, it is possible to employ: oxide of alkaline earth metal such as calcium (Ca), magnesium (Mg), strontium (Sr), barium (Ba), and beryllium (Be); oxide of alkali metal such as sodium (Na), potassium (K), rubidium (Rb), and cesium (Cs); and oxide of rare earth such as scandium (Sc), yttrium (Y) and the lanthanoids.

Figure 14:
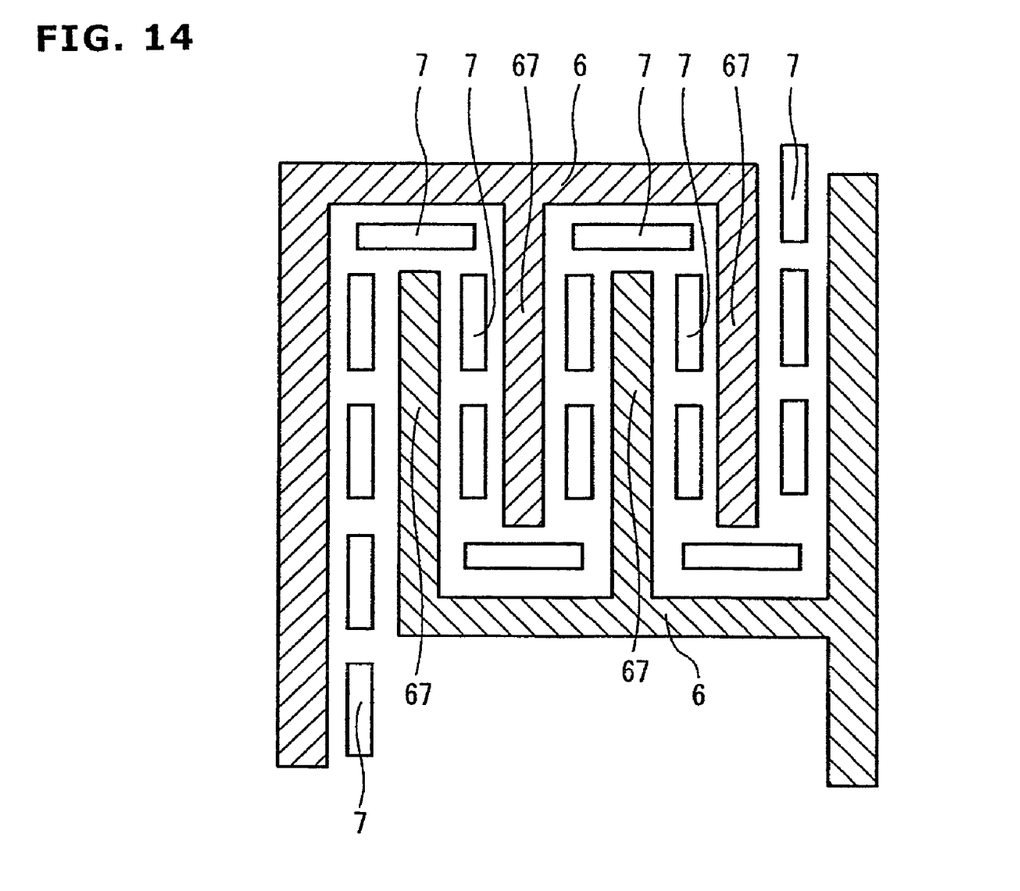
FIG. 14 is a sectional view taken across the line C-C shown in FIG. 2 as viewed in the direction of arrows, showing the gas sensor 1 in a first variation example of the adhesion layer 7.
Figure 15:
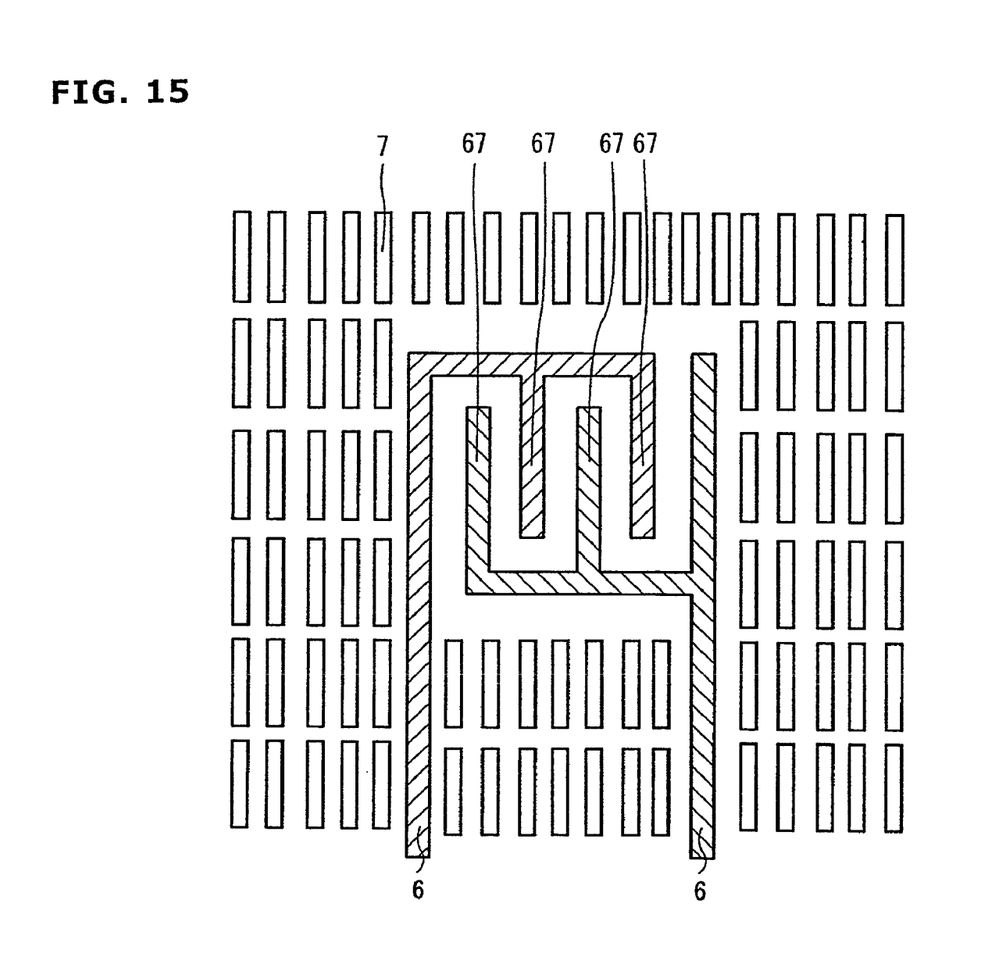
FIG. 15 is a sectional view taken across the line C-C shown in FIG. 2 as viewed in the direction of arrows, showing the gas sensor 1 in a second variation example of the adhesion layer 7.

The shape of adhesion layer 7 is not limited to the above-mentioned embodiment. The adhesion layer 7 can be constructed in one of the following variations as shown in FIG. 14 and FIG. 15. Except for the construction of adhesion layer 7, the construction of gas sensor 1 in each of the following variation examples is the same as that of the above-mentioned first embodiment, so that repetitive explanation is omitted. The up and down direction is the up and down direction as viewed in FIGS. 14~16, and the left and right direction is the left and right direction as viewed in FIGS. 14~16.

As shown in FIG. 14, the adhesion layer 7 of the first variation example is shaped, as viewed in a plan view, in the form of strips or rectangles, and composed of a plurality of segments which are separated from one another and which are arranged in a row between the teeth 67 of one sensing electrode 6 and the teeth 67 of the other sensing electrode 6. The adhesion layer 7 is arranged so as to be out of contact with sensing electrodes 6.

As shown in FIG. 15, the adhesion layer 7 of the second variation example is shaped, as viewed in a plan view, in the form of strips or rectangles, and composed of a plurality of segments which are separated from one another and which are arranged in an array so as to surround one sensing electrode 6 and the other sensing electrode 6. The s adhesion layer 7 is arranged so as to be out of contact with sensing electrodes 6.

Figure 16:
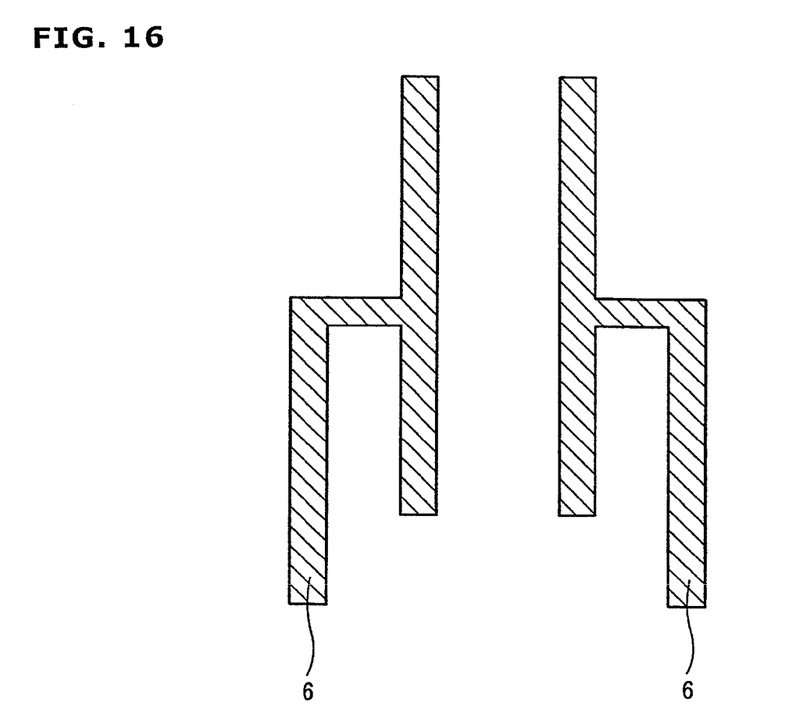
FIG. 16 is a sectional view taken across a line C-C shown in FIG. 2 as viewed in a direction of arrows, showing the gas sensor in a variation example of the sensing electrodes 6.

The following is explanation on a variation example of the sensing electrodes 6 with reference to FIG. 16, in which the adhesion layer 7 is omitted. Instead of being shaped like a comb, the sensing electrodes 7 of this variation example are symmetrically formed, as shown in FIG. 16, in the form of parallel electrodes each having a top segment confronting the top segment of the other electrode with a predetermined gap, and a bottom segment which is bent. In this case, it is possible to employ any of the above-mentioned shapes and configurations of adhesion layer 7.

In the above-mentioned embodiment and variation examples, preferably, the projected area of the contact surface between the gas sensing layer 4 and adhesion layer 7, projected from the gas sensing layer's side on the base member 15 is equal to or greater than 50% of the projected area of the contact surfaces of the gas sensing layer 4, the adhesion layer 7 and the sensing electrodes 6, projected from the gas sensing layer's side on the base member 15. With this construction, it is possible to achieve the adhesion between the base member 15 and gas sensing layer 4 more securely. In the above-mentioned embodiment, the gas sensor 1 is so constructed that the projected area obtained by projecting the contact surface between the adhesion layer 7 and the gas sensing layer 4 on the base member 15 becomes equal to 68% of the projected area obtained by projecting the contact surfaces of the gas sensing layer 4 with the adhesion layer 7 and the sensing electrodes 6 on the base member 15.

Figure 17:
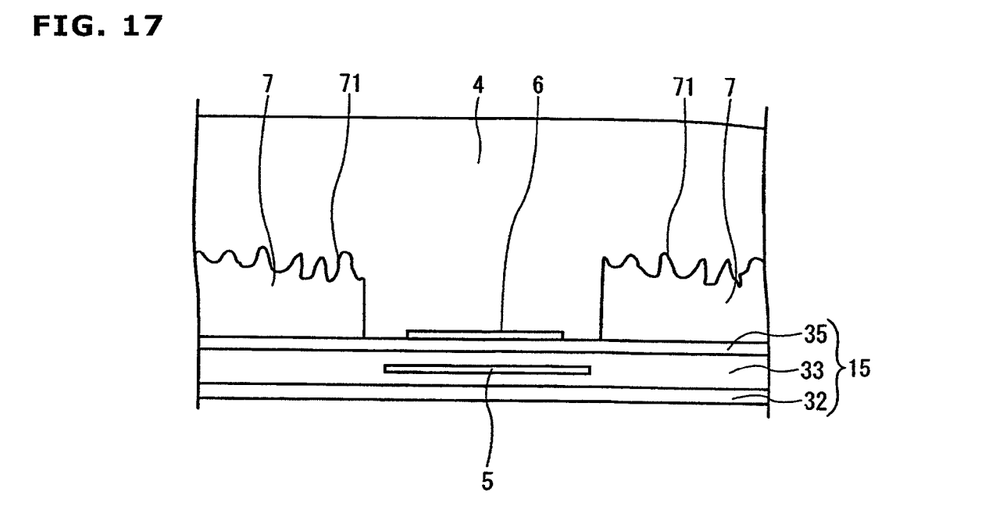
FIG. 17 is an enlarged partial sectional view taken across the line A-A shown in FIG. 1 as viewed in the direction of arrows, showing the vicinity of a gas sensing layer 4.

The following is explanation on a variation example of the thicknesses of gas sensing layer 4 and base member 15 with reference to FIG. 17. In this variation, as shown schematically in FIG. 17, the adhesion layer 7 is made thicker than the sum of the thicknesses of insulating layers 32 and 33 and protection layer 35, and made higher in the degree of irregularity or ruggedness. The degree of irregularly of adhesion layer 7 tends to increase as the thickness of adhesion layer 7 increases.

The production method of producing gas sensor 1 of this variation example is the same as the production method of the above-mentioned embodiment except that, in (9) "Forming adhesion layer 7", the thickness of adhesion layer 7 is increased by adjusting the amount of film deposition of the hillock Al film, and the degree of irregularity of adhesion layer 7 is increased. The insulating layers 32 and 33 and protection layer 35 are made in the form of thin film and the thickness is smaller than or equal to 2 μm, more specifically the thickness is 600 nm. The adhesion layer 7 is formed thicker than the insulating layers 32 and 33 and protection layer 35, so that adhesion layer 7 is capable of preventing deflection of the thin formed insulating layers 32 and 33 and protection layer 35.

Figure 19:
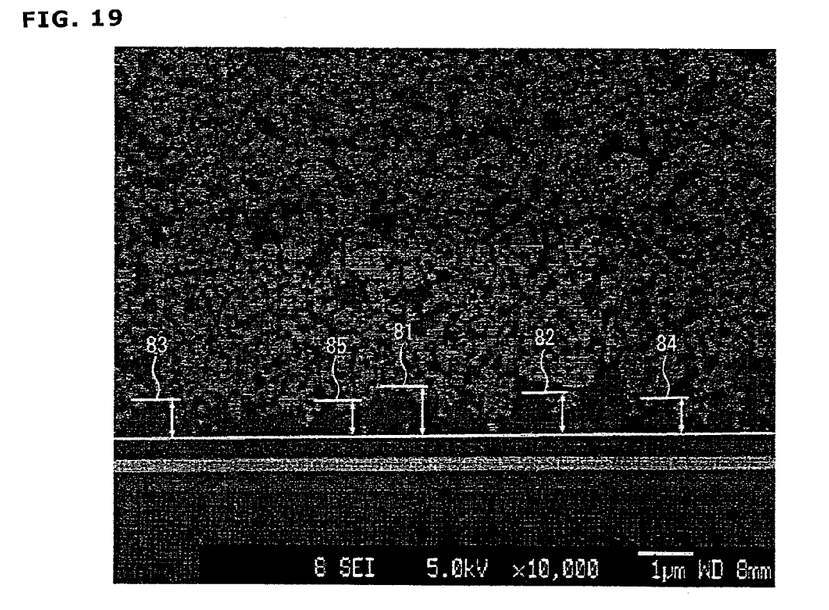
FIG. 19 is a view showing a magnified image of a section of the gas sensor taken by a scanning electron microscope to show the state of the adhesion layer of the gas sensor in the variation example.

To check the condition of adhesive layer 7 in gas sensor 1 of this variation example, gas sensor 1 was cut in the thickness direction of silicon substrate 2 so as to include adhesion layer 7, and the section of adhesion layer 7 obtained by an intersecting plane extending in the thickness direction was observed by a scanning electron microscope in a magnified scale 10000 times larger than the actual size. FIG. 19 shows a magnified photographic image of adhesive layer 7 obtained by the scanning electron microscope. From FIG. 19, it is confirmed that the surface of adhesive layer 7 is in the form of irregular surface 71 having convexities and concavities. To confirm the degree of irregularity of adhesive layer 7, among heights of peaks forming convex portions or convexities of adhesive layer 7, from the surface of protection layer 35 (the rectilinear distance in the direction perpendicular to the surface of protection layer 35), the mean of the heights of the five highest or tallest peaks 81~85 was calculated. As a result, this mean is greater than the total thickness (600 nm) of insulating layers 32 and 33 and protection layer 35. In this way, by making the above-mentioned mean of adhesive layer 7 greater than the total thickness of insulating layers 32 and 33 and protection layer 35, it is possible to further improve the adhesion between gas sensing layer 4 and base member 15. In this variation example, the thickness (means thickness) of gas sensing layer 4 was equal to about 15 μm as in the above-mentioned embodiment, and the surface roughness Ra of protection layer 35 was 0.002 μm.

Figure 18:
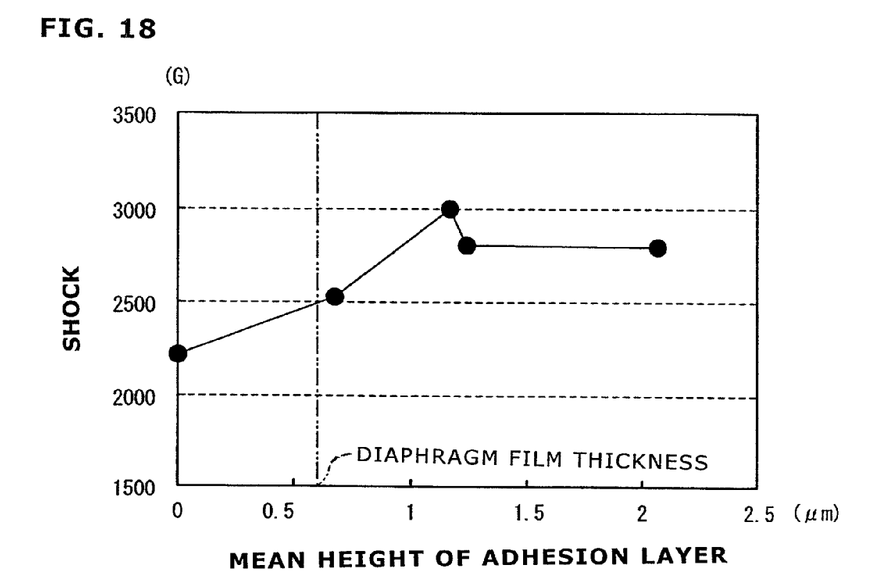
FIG. 18 is a graphic view showing the results of shock test.

With reference to a graph shown in FIG. 18, the results of a shock test of gas sensor 1 is explained in the following. The shock test was performed by preparing five samples in which the total thickness of insulating layers 32 and 33 and protection layer 35 was 0.6 μm (600 nm), the adhesive layer 7 was made of alumina ($Al_2O_3$), and the degree of irregularity of adhesive layer 7 was adjusted appropriately. After the shock test, the mean height of the five peaks 81~85 of convex portions of adhesive layer 7 from the surface of protection layer 35 was calculated for each of the five samples by using the above-mentioned calculation method. As a result, the means heights of adhesive layers 7 formed in these samples are: 0.010 μm, 0.672 μm, 1.168 μm, 1.238 μm and 2.067 μm. The shock test was performed by using a shock test machine SM-110-MP (model name) manufactured by AVEX corporation.

According to the results of this shock test, in the case of the above-mentioned mean thickness of adhesive layer 7 being equal to 0.010 μm, the gas sensing layer 4 was not separated from base member 15 up to 2214 G. In the case of the means thickness of adhesive layer 7 being equal to 0.672 μm, the gas sensing layer 4 was not separated from base member 15 up to 2500 G. In the case of the means thickness of adhesive layer 7 being equal to 1.168 μm, the gas sensing layer 4 was not separated from base member 15 up to 3000 G. In the case of the mean thickness of adhesive layer 7 being equal to 1.238 μm, the gas sensing layer 4 was not separated from base member 15 up to 2806 G. In the case of the mean thickness of adhesive layer 7 being equal to 2.067 μm, the gas sensing layer 4 was not separated from base member 15 up to 2794 G. Therefore, the gas sensor including adhesive layer 7 having the mean thickness greater than the total thickness of the insulating layers 32 and 33 and protection layer 35 can withstand shock greater than or equal to 2500 G, and the adhesion can be improved dramatically between gas sensing layer 4 and base member 15.

INDUSTRIAL APPLICABILITY

The present invention is applicable to semiconductor gas sensors.

The invention claimed is:

1. A gas sensor comprising:
a gas sensing layer which is formed on a base member and which includes, as a main component, a metal oxide semiconductor having an electric characteristic varied in accordance with variation of a concentration of a specific gas in a measurement gas;
characterized in that the gas sensor further comprises:
a pair of sensing electrodes formed on the base member and arranged to sense variation of the electric characteristic of the gas sensing layer; and
an adhesion layer contacting with the gas sensing layer;
the sensing electrodes being in contact with the gas sensing layer, but not in contact with the adhesion layer; and
that the base member includes:
a semiconductor substrate formed with an opening portion extending in a thickness direction,
an insulating layer which is formed on the semiconductor substrate and which includes a separating wall portion formed at a position confronting the opening portion,
a heat generating resistor formed on the separating wall portion, and
a protection layer formed on the insulating layer to cover the heat generating resistor; and
the sensing electrodes, the adhesion layer, and the gas sensing layer being formed on the protection layer of the base member.

2. The gas sensor as recited in claim 1, wherein the sum of thicknesses of the insulating layer and the protection layer is smaller than or equal to 2 μm, a surface roughness Ra of a surface of the protection layer is smaller than or equal to 0.030 and the gas sensing layer having a thickness greater than 2 μm is formed on the surface of the protection layer.

3. The gas sensor as recited in claim 1, wherein a mean of five greatest peak heights among heights of surface roughness peaks forming convexities of a surface of the adhesion layer from the surface of the protection layer as viewed in a section extending in a thickness direction of the adhesion layer is greater than the sum of thicknesses of the insulating layer and the protection layer.

4. The gas sensor as recited in claim 3, wherein the sum of thicknesses of the insulating layer and the protection layer is smaller than or equal to 2 μm, a surface roughness of a surface of the protection layer is smaller than or equal to 0.030 μm, and the gas sensing layer having a thickness which is greater than 2 μm and which is equal to or greater than the double of the sum is formed on the surface of the protection layer.

5. The gas sensor as recited in claim 1, wherein the adhesion layer is formed at least between the sensing electrodes.

6. The gas sensor as recited in claim 1, wherein the sensing electrodes are formed in the shape of a comb, a tooth of one of the electrodes is inserted between teeth of the other of the electrodes, and the adhesion layer is formed between the teeth of one of the electrodes and the teeth of the other of the electrodes.

7. The gas sensor as recited in claim 1, wherein the adhesion layer is formed continuously between the sensing electrodes and around the sensing electrodes.

8. The gas sensor as recited in claim 1, wherein the adhesion layer is an insulating layer.

9. The gas sensor as recited in claim 1, wherein a material of the gas sensing layer is inserted between particles of a material of the adhesion layer.

10. The gas sensor as recited in claim 1, wherein a projected area obtained by projecting a contact surface between the gas sensing layer and the adhesion layer from a gas sensing layer's side on which the gas sensing layer formed the base member is located occupies a percentage greater than or equal to 50% of a projected area obtained by projecting a contact surface between the gas sensing layer and the adhesion layer and sensing electrodes from the gas sensing layer's side on which the gas sensing layer formed the base member is located.

* * * * *